United States Patent [19]

Bellis et al.

[11] Patent Number: 5,138,074

[45] Date of Patent: Aug. 11, 1992

[54] CONTINUOUS CATALYZED VAPOR PHASE DIMERIC CYCLIC ESTER PROCESS

[75] Inventors: Harold E. Bellis, Wilmington; Kamlesh K. Bhatia, Newark, both of Del.

[73] Assignee: E. I. Du Pont de Nemours and Company, Wilmington, Del.

[21] Appl. No.: 545,379

[22] Filed: Jun. 28, 1990

[51] Int. Cl.$^5$ .................. C07D 319/12; C07D 321/00
[52] U.S. Cl. .................... 549/274; 549/267; 549/296; 549/319
[58] Field of Search .............. 549/274, 267, 296, 319

[56] References Cited

U.S. PATENT DOCUMENTS

| | | | |
|---|---|---|---|
| 1,095,205 | 5/1914 | Gruter et al. | 549/274 |
| 2,668,162 | 2/1954 | Lowe | 549/274 |
| 4,835,294 | 5/1989 | Seebach et al. | 549/274 |

FOREIGN PATENT DOCUMENTS 0264926  4/1988  European Pat. Off. .
0261362  10/1988  Fed. Rep. of Germany .

Primary Examiner—C. Warren Ivy
Assistant Examiner—Amelia A. Owens
Attorney, Agent, or Firm—Charles E. Krukiel

[57] ABSTRACT

A continuous catalyzed vapor phase process for the production of dimeric cyclic esters which comprises converting the corresponding alpha-hydroxy-carboxylic acid or ester in the vapor phase over a solid catalyst, such as a silica-alumina, preferably a silica-alumina having a high silica content, in the presence of a carrier of gas.

20 Claims, 2 Drawing Sheets

CONTINUOUS CATALYZED VAPOR PHASE DIMERIC CYCLIC ESTER PROCESS

FIELD OF THE INVENTION

This invention relates to a continuous process for preparing dimeric cyclic esters by thermolysis of alpha-hydroxycarboxylic acids or esters thereof in the vapor phase in the presence of a solid catalyst. More particularly, the invention relates to a gas-assisted atmospheric pressure process that provides for the rapid conversion of the carboxylic material to the cyclic ester. More specifically, it relates to the production of glycolide and lactide by such process.

BACKGROUND OF THE INVENTION

The preparation of cyclic esters of alpha-hydroxycarboxylic acids is an old and much studied process. Heretofore, the preparation has been conducted in two distinct batch steps involving first preparing an oligomer of the hydroxycarboxylic acid, i.e., a relatively short-chain condensation polymer thereof, then heating the polymer under reduced pressure to generate the desired cyclic ester. Gruter et al., U.S. Pat. No. 1,095,205 (1914); Lowe, U.S. Pat. No. 2,668,162 (1954); Bhatia, U.S. Pat. No. 4,835,293 (1989); Bellis, U.S. Pat. No. 4,727,163 (1988); Muller, Ger. Pat. Applications 3632103 and 3708915 (1988). Such processes spanning over 70 years of technology suffer in that they require hours of reaction time at high temperatures for the preparation of the polymeric intermediate and its thermolysis to the cyclic ester. Further, the rather long residence times at the high temperatures employed often results in side reactions leading, for example, to unwanted isomers, charring of the polymer and consequently difficult to handle reactor heels.

It is an object of this invention to provide a novel essentially single-step continuous process for the rapid conversion with high productivity of an alpha-hydroxycarboxylic acid or ester thereof to a cyclic ester in a single reaction zone without need to separately prepare an oligomer intermediate to the cyclic ester.

It is another object to provide such a process that is conducted with the carboxylic acid material being fed in the vapor phase to a reaction zone containing a solid catalyst for the conversion to the dimeric cyclic ester.

Still another object is to provide a process as above that is gas-assisted, the gas serving to facilitate the feeding of the carboxylic material to the reaction zone as well as the removal of the resultant cyclic ester therefrom.

Yet another object is to provide such continuous catalyzed vapor phase process for the production of glycolide and lactide, in particular L-lactide from L-lactic acid or an alkyl lactate.

SUMMARY OF THE INVENTION

A continuous catalyzed vapor phase process for converting an alpha-hydroxycarboxylic acid or ester to a dimeric cyclic ester, which process comprises
(i) continuously vaporizing the hydroxycarboxylic material and feeding it to a reaction zone containing a solid catalyst effective to oligomerize and cyclize the carboxylic material to the cyclic ester,
(ii) maintaining the reaction zone at a temperature and pressure effective to result in the formation of the cyclic ester and maintain it in the vapor phase, and
(iii) recovering the cyclic ester from the vapor phase.

In a preferred embodiment, a carrier substance gaseous and non-reactive at said temperature and pressure is continuously fed to the reaction zone to form a gas feed stream containing the carboxylic material and a gas product stream containing the cyclic ester, and the cyclic ester is recovered from the gas product stream.

In another preferred embodiment, the gaseous carrier substance is employed to assist in vaporizing the carboxylic material as well as to carry it into the reaction zone for contact with the solid catalyst.

Still other embodiments include operating at at least about atmospheric pressure, preferably at about atmospheric pressure; employing an alkyl glycolate feed to prepare glycolide and a lactic acid or an alkyl lactate feed to prepare a lactide, preferably an L- or D- lactide from an L- or D- lactic or lactate feed material; employing selected highly effective silica and alumina-based catalysts for the production of the desired cyclic esters; and employing the catalyst in particulate form as a substantially fixed or fluidized bed.

Under the invention conditions, formation of the cyclic ester is rapid. Although the mechanism of the reaction is not completely known, it is believed that it proceeds to form the cyclic ester directly from the monomeric carboxylic feed material itself or from a transient, intermediately formed low molecular weight oligomer thereof. Thus, the invention process offers numerous advantages over the art. It substantially reduces the time required for converting an alpha-hydroxycarboxylic-based feed material as defined into the desired cyclic ester. In contract to the prior processes, which require hours for such conversion, the subject process can produce a cyclic ester such as lactide in much less time. As a consequence of the continuous feed, product take-off and gas sweeping features, in combination with effective reaction temperatures, the formation and accumulation of a distinct reaction mass phase on the surface of the catalyst can be minimized so that loss of potential cyclic ester yield through degradation reactions and/or coating of the catalyst can also be minimized.

Further, operating at pressures of about atmospheric reduces investment and operating costs, by eliminating the costly equipment required for maintaining the low reduced pressures utilized in the art. It also provides for a safer operation, particularly in combination with a cyclic ester stripping gas. The stripping gas, at atmospheric and higher, eliminates the potential for explosive atmospheres within the reactor that can result from air leaks, especially at reduced pressures.

DETAILED DESCRIPTION OF THE INVENTION

Figure 1:
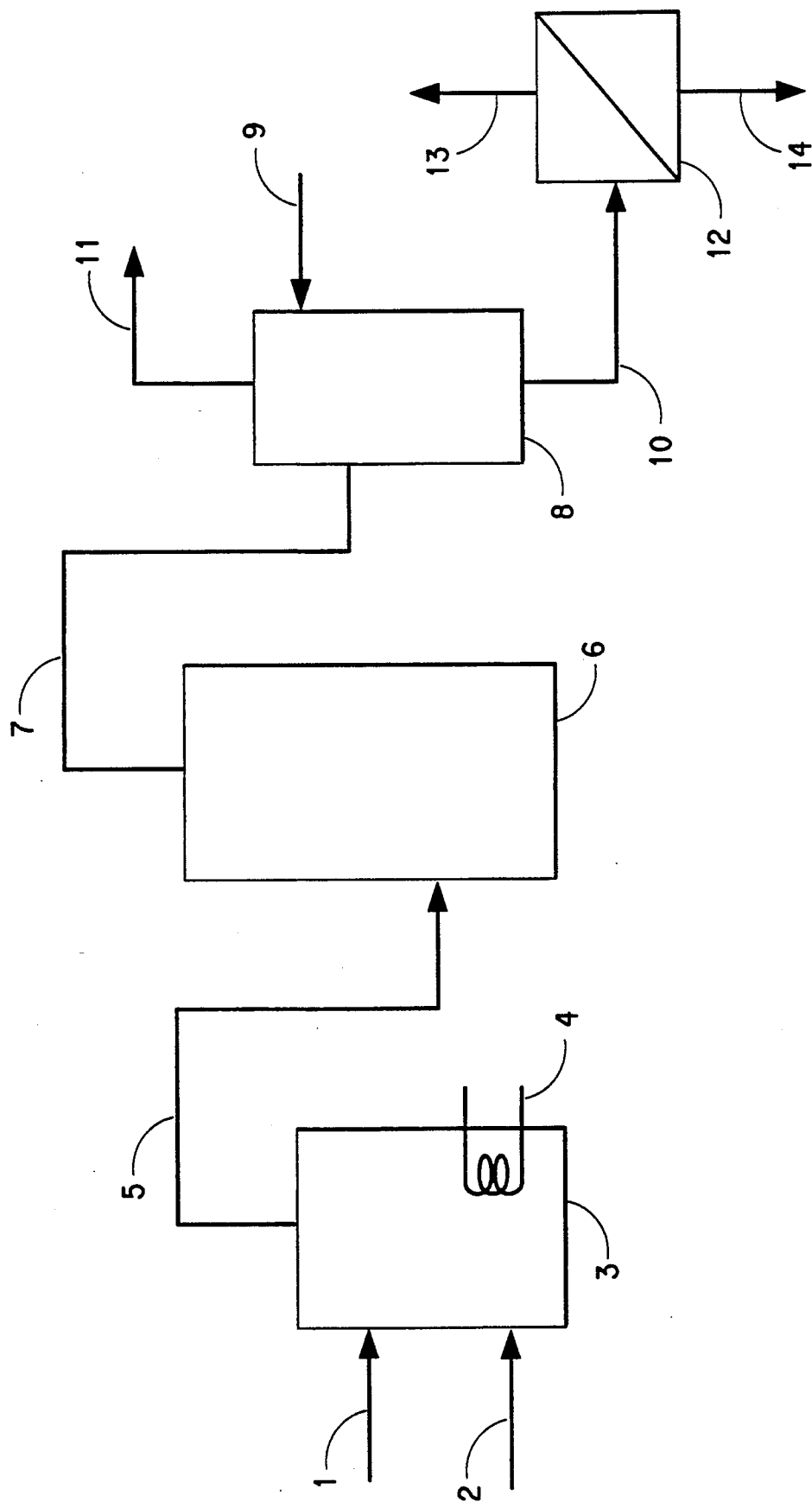

In general, the process is conducted by continuously introducing an alpha-hydroxycarboxylic acid or ester thereof in the vapor state into a reaction zone containing a solid catalyst and maintained at a temperature effective to convert the carboxylic material to a cyclic ester and to vaporize it. Substantially simultaneously a substantially continuous flow of a gaseous carrier substance as defined is preferably passed into the reaction zone assist in carrying the carboxylic material to the catalyst sites and to carry reaction products away from the catalyst sites and out of the reaction zone as a gaseous product stream. The gaseous product stream removed from the reaction zone contains the cyclic product along with other components, for example. in the case of an aqueous lactic acid feed, the free water, the water of reaction, unconverted lactic acid and/or open chain dimer or trimer. The cyclic ester may be recovered from the product stream by any of the methods known in the art, including solvent-scrubbing. One such solvent-scrubbing method is disclosed in Bhatia U.S. Pat. No. 4,835,293, which disclosure is incorporated herein by reference. Unreacted carboxylic feed material and/or open chain dimers and trimers thereof can be recycled to the reaction zone, either alone or in conjunction with fresh starting material.

Preferably, the carboxylic material is fed to the reaction zone as a vaporized component of a gas feed stream comprising it and an inert gaseous carrier substance described more fully below.

It is to be understood that the term "continuous feed" as used herein is meant to include pulsed (intermittent) as well as constant feed. Also, by the term "vaporizing" the carboxylic material is meant to include providing it to the reaction zone as a spray of fine liquid droplets or mist obtained by atomizing or spraying the material into the reaction zone, or as a finely divided solid as well as by heating the material to its boiling point at the operating pressure or by entraining its vapors in a stream of a carrier gas at a temperature below its boiling point at which it exerts a significant vapor pressure.

The alpha-hydroxycarboxylic feed material can vary widely as to composition provided it is vaporizable and capable of forming the corresponding cyclic ester. Included are open-chain aliphatic hydroxycarboxylic acids and esters thereof having the formula, $HOCRR_2COOR_3$, where $R_1$, $R_2$ and $R_3$ can independently be hydrogen or a $C_1$-$C_6$ aliphatic hydrocarbyl radical. Preferably $R_1$, $R_2$ and $R_3$ when other than hydrogen are $C_1$-$C_4$ alkyl groups. More preferably, $R_1$ and $R_2$ are H or methyl as in glycolic acid ($R_1$=$R_2$=H) and lactic acid ($R_1$=H, $R_2$=$CH_3$). Since glycolic acid is not readily vaporizable as such it is conveniently fed to the reaction zone as an ester, e.g., methyl glycolate. Lactic acid may be fed as the free acid, including as an aqueous solution such as the 88% aqueous composition available commercially, or as an ester, e.g., methyl or butyl lactate.

The overall process may be represented schematically as follows:

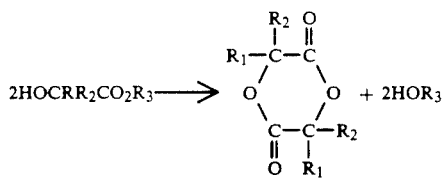

where $R_1$, $R_2$ and $R_3$ are as defined above.

The hydroxycarboxylic acid or ester feed material may be fresh material or it may be a vaporized process stream from a cyclic ester process that contains such unreacted open-chain material along with the cyclic ester product. Such process stream may, for example, be a gas product stream formed in the gas-assisted cyclic ester process described in Bhatia U.S. Pat. No. 4,835,293, which stream may contain an alpha-hydroxylic acid such as lactic acid and low molecular weight oligomers thereof in addition to the lactide product. Such stream may be treated directly in accordance with the method of the present invention to convert its open-chain lactic acid and oligomer content to additional lactide before the gas stream is subjected to a product work-up procedure such as the solvent-scrubbing method of the referenced Bhatia patent. In this way, the overall conversion of the patented process could be increased.

The process is conducted in the presence of a solid catalyst, which may be any of those known in the art for promoting condensation of the alpha-hydroxycarboxylic component to oligomer and for promoting cyclic ester formation. The catalyst will normally be particulate, so as to present a high surface area and disposed as a bed in the reaction zone.

The catalysts for the present purpose are generally metals of groups III, IV, V and VIII of the Periodic Table on compounds of the metals such as the oxides, halogenides and carboxylates. Typical are tin as the metal (powdered), oxide (SnO) or carboxylate (Sn II octoate); antimony, usually as the trivalent oxide ($Sb_2O_3$). Other suitable catalysts are silica ($SiO_2$); alumina ($Al_2O_3$); and titania ($TiO_2$). These materials may be employed singly or as mixtures, and may be unsupported solids or supported on a solid carrier, which may or may not in itself be catalytic for the present purpose. Typical supports include alumina, silica, titania and carbon.

Supported catalysts may be made by any of the methods known in the art, including impregnating or coating the support with a solution or slurry of the catalytic agent in a suitable solvent, separating the coated and/or impregnated support from the solvent and drying, including spray drying, for solvent removal, and if desired commuting the solid product further if desired.

One particularly suitable catalyst class comprises compositions composed essentially of silica and alumina, commonly referred to as silica-aluminas or aluminosilicates. These compositions may contain 1-99% by weight of silica and 99-1% by weight of alumina. Included are high alumina content silica-aluminas containing, for example, 1-13% $SiO_2$ and 99-87% by weight $Al_2O_3$, preferably 3-10% $SiO_2$ and 97-90% $Al_2O_3$. On such composition available commercially is Harshaw Al-1602 containing 6% $SiO_2$ and 94% $Al_2O_3$.

Highly preferred are the high silica compositions such as those containing a major proportion of silica, preferably 80-90% silica. Representative is a catalytic composition consisting essentially of 86% $SiO_2$ and 14% $Al_2O_3$ which is commercially available as Akzo LA-30. Another consists essentially of 85% $SiO_2$ and 17% $Al_2O_3$, commercially available as Davison D-970.

The silica-alumina catalysts can be made by the well-known method of co-precipitating appropriate amounts of sodium silicate and sodium aluminate from aqueous solution by adjusting the pH of the solution to about 8 with hydrochloric acid at 50°-70° C. The resulting gel, a mixture of hydroxides, is recovered, washed free of chlorides and dried to a free-flowing powder, pelleted and then calcined at 450°-650° C. to give a material which can be used directly as the catalyst.

Pellet size, pore volume and total surface area may vary widely. Typical pellet sizes are in the range of from about 3 to 300 mm, pore volumes from about 0.2 to 0.8 u/g and total surface area from about 100 to 250 m²/g. For example, pellets of the preferred 86% $SiO_2$—14% $Al_2O_3$ catalyst composition described above have an average diameter of 4.2 mm, a pore volume of 0.53 mm, a total surface area of 135 m²/g and a bulk density of 0.68 g/ml.

In still another suitable catalyst class are compositions comprising alumina and titania, commonly referred to as aluminotitanates, with alumina generally present in predominating amounts. Typically such compositions contain about 0.1-20% titania and 99.9-80%, by weight, alumina, usually 0.2-10% titania and 99.8-90% alumina, including about 1% titania and about 99% alumina. The titania can be present as a coating on the alumina or uniformly distributed throughout the composition. They can be prepared by mixing aqueous solutions of $TiCl_4$ and sodium aluminate in proportions pre-calculated to give the desired titania/alumina ratio and adjusting the solution pH to about 8 at 50°-70° C. The resulting gel is recovered, washed free of chlorides with water, dried to a powder, shaped and calcined at 450°-650° C. to give a material that can be used directly herein as the catalyst.

Such catalysts typically have sizes usually in the range of 2-120 mm in all directions. Pore volume, pore size and total surface area generally range from about 0.2-0.8 ml/g, greater than 25 Angstrom units and 100-250 $m^2$/g, respectively.

The gaseous agent for carrying the hydroxycarboxylic feed material into the reaction zone and for carrying the cyclic ester, water (or alcohol) of reaction and any unreacted feed material out of the reaction zone may be any substance that is gaseous and stable at the operating temperatures and pressures and is inert to the starting material and reaction products. It may be normally gaseous, such as nitrogen, argon, carbon monoxide or dioxide or low molecular weight hydrocarbon. It may be normally non-gaseous but gaseous at reaction temperature and pressure. Preferred is nitrogen for its inertness and ready availability. Preferably the gas will be preheated to or reasonably close to the operating temperature.

The ratio of the amount of gas to the amount of the carboxylic feed material should be such as to ensure that substantially all the feed material is vaporized at the operating temperature and pressure and that the reaction products are in the vapor phase as well. The relative quantities of gas to feed components and reaction products as well as the optimum gas flow, which may vary with any particular combination of feed material, catalyst, catalyst particle size, temperature and the degree of conversion desired can be readily determined by trial.

Suitably effective temperatures for converting the alpha-hydroxycarboxylic component can also vary widely. It should be sufficiently high to provide the starting material in the vapor state at the operating pressure, but not so high as to result in its degradation. It should also be at or above the depolymerization temperature of any intermediately formed oligomer of the hydroxycarboxylic material fed to the reaction zone to ensure rapid depolymerization of such material to cyclic ester on the surface of the catalyst and to avoid or minimize possible undue accumulation of deposits on the catalyst. Further, the temperature should be sufficiently high to provide and maintain the cyclic ester in the vapor state.

The temperature will normally be in the 170° to 270° C. range depending on the particular hydroxycarboxylic acid or ester employed. With methy glycolate, for example, from 230° to 260° C. is preferred; with lactic acid and its esters from about 190° to 230° C. is preferred, more particularly from about 200° to 220° C.

The pressure may vary from sub-atmospheric to atmospheric and super-atmospheric. Preferably it is about atmospheric, plus a small back pressure exerted on the product stream by the downstream equipment which should be designed to keep the back pressure as low as practical, for example to keep the back pressure as low as 5 psig.

The reactor design and configuration are not critical provided they provide a reaction zone that can accommodate a mass of solid catalyst, for example, as a bed of particulate material or as a coating on the walls thereof, has means for feeding vaporized carboxylic feed material and preferably also a gaseous carrying agent for bringing the feed material into contact with the catalyst and has means for removing the reaction products from the reaction zone, preferably as a gas product stream. The reactor may be of any design known in the art for effecting gas-solid contact such as a fixed bed or a tubular reactor. It may also be a fluidizable bed reactor in which the carrier gas of the present invention serves to maintain the bed fluidized.

An embodiment of a fluidized bed could be a moving bed reactor in which the catalyst is continuously removed from the reactor with the gaseous product stream containing the cyclic ester, separating the catalyst particles from the gas stream (for example, with a cyclone separator), recycling the catalyst to the reactor and recovering the cyclic ester from the gaseous product stream by solvent scrubbing as described in FIG. 1.

Likewise, the product stream recovery and processing system may be any of those known in the art. One such product recovery system is disclosed in Bhatia U.S. Pat. No. 4,835,293, which disclosure is incorporated herein by reference. The invention is further illustrated with reference to the accompanying figures.

FIG. 1 schematically depicts the overall invention process conducted in a continuous manner at about atmospheric pressure in a reactor system comprising a vaporizer, a catalytic reactor and a product recovery device.

Figure 2:
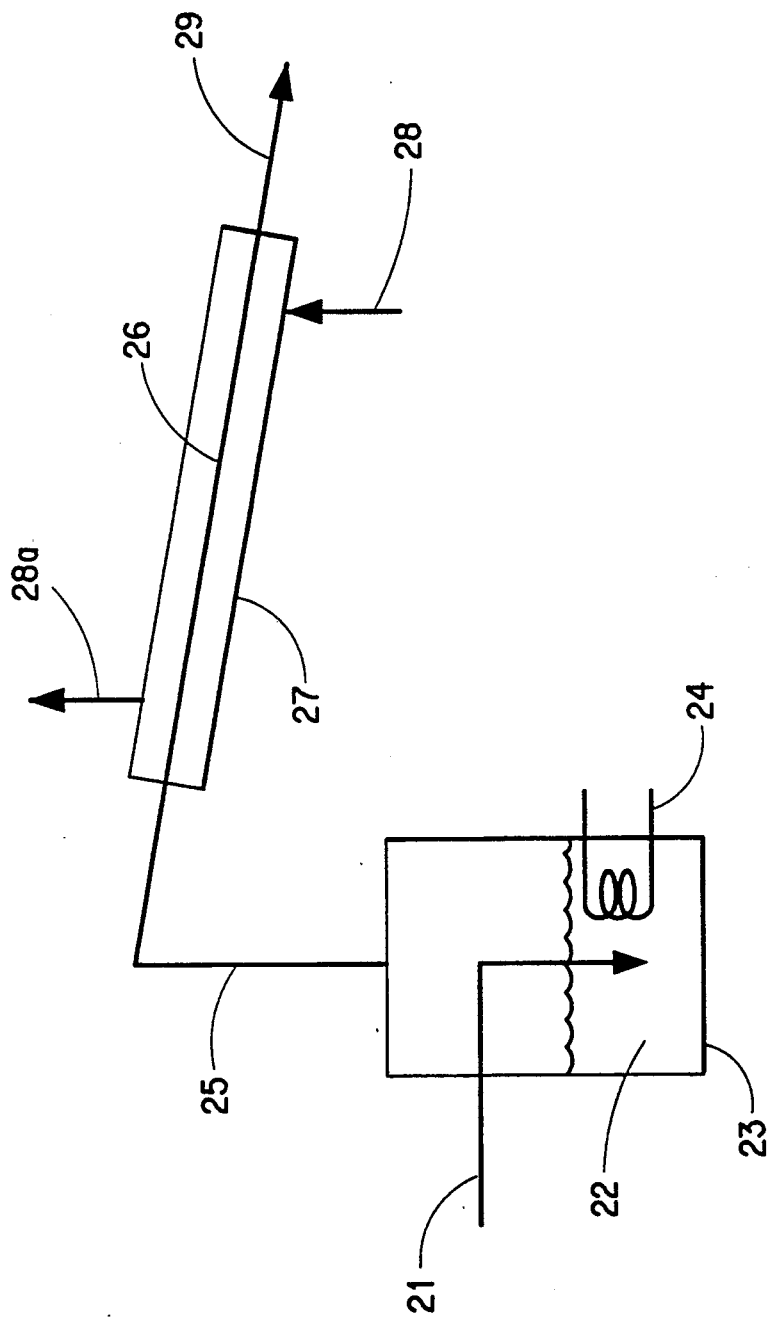

FIG. 2 further depicts the FIG. 1 system wherein the catalytic reactor has a packed bed tubular reactor zone.

With reference to FIG. 1, a vaporizable hydroxycarboxylic feed material, such as methyl glycolate, is fed continuously through line 1 into vaporizer 3 equipped with heater 4. Simultaneously $N_2$ gas is continuously fed to 3 through line 2 while the feed material is heated to a vaporizing temperature at which it exerts a significant vapor pressure. The $N_2$ methyl glycolate vapor stream passes through line 5 to the lower end of reactor 6 containing a bed of catalyst (not shown) and heated to a temperature effective to convert the feed material (methyl glycolate) to dimeric cyclic ester (glycolide) and by-product water or alcohol (methanol), e.g., to 240° C. for glycolide production. The resulting gaseous reaction product stream comprising $N_2$, cyclic ester (glycolide), alcohol (methanol) and unreacted feed material (methyl glycolate), if any, leaves 6 through line 7 and passes into solvent scrubber 8 containing a scrubbing solvent, such as isopropyl alcohol (IPA), entering the scrubber from 9, maintained at a temperature at which cyclic ester crystallizes from the solvent as disclosed in Bhatia, U.S. Pat. No. 4,835,293. The solvent-scrubbing action produces a slurry of solid cyclic ester (glycolide) particle in IPA. The slurry is removed through line 10 and filtered in filter 12. Solid cyclic ester (glycolide) is removed from the filter through 13, the filtrate through 14. The cyclic ester (glycolide) can be further purified if necessary by any means known in the art, including by the further treatments disclosed in the referenced Bhatia patent.

With reference to FIG. 2, a hydroxycarboxylic feed material, such as n-butyl lactate, is continuously fed through line 22, while $N_2$ gas is continuously fed through 21, into vaporizer 23 heated by heater 24. The resulting gas stream bearing vaporized feed material (butyl lactate) exits 23 through line 25 and passes into tubular reaction zone 26 surrounded by jacket 27 and packed with a bed of catalyst particles (not shown). Reaction zone 22 is heated to a cyclic ester-generating temperature (about 216° C. for lactide) by means of a heating fluid, which enters jacket 27 at inlet 28 and exits at 28a. The $N_2$-cyclic ester (lactide) gas product stream also containing by-product alcohol (butanol) and unreacted feed material (butyl lactate) exits the reaction zone through line 29 and passes to a recovery zone (not shown), which may be as described on FIG. 1.

With further reference to FIG. 2, Bhatia, U.S. Pat. No. 4,835,293 describes a gas-assisted process for depolymerizing oligomers to dimeric cyclic esters. The resulting gas product stream contains dimeric cyclic ester accompanied by by-product alpha-hydroxycarboxylic acids. Such gas product stream may be used directly in the method of the present invention as the carboxylic feed stream in the embodiment illustrated in FIG. 2.

A similar gas process stream can be produced by heating lactic acid, including aqueous lactic acid, in a stream of a carrier gas in the presence of a catalyst, such as $Sn^{II}$ octoate, at a temperature effective to result in the formation of an intermediate oligomer of the acid and to subsequently depolymerize it to lactide. The thus produced gaseous product stream normally contains, in addition to lactide, substantial quantities of hydroxycarboxylic acids, mainly lactic acid accompanied by lesser amounts of its open-chain dimer and trimer. Such gaseous product stream can also be used as the feed stream for the conversion of the hydroxylcarboxylic acids contained therein to lactide in accordance with the invention embodiment illustrated in FIG. 2.

EXAMPLE

With reference to FIG. 2, a gaseous $N_2$ stream containing an organic mixture of 80% lactide, 15% lactic acid and 5% higher hydroxy acids produced by the sequential dehydration-polymerization-depolymerization of 88% aqueous lactic acid is fed at a flow rate of 0.3 standard cubic feed per minute into a jacketed tubular catalytic reactor essentially as described in FIG. 2. Tubular reaction zone 26, 400 mm in length with an inside diameter of 25 mm, containing 90 g of a 2% by weight stannous oxide on carbon catalyst, and is heated to 216° C. by circulating vapors of boiling dodecane through jacket 27 surrounding the reaction zone. The composition of the gas stream before and after entering the reactor is determined gas chromatographically. The gas chromatographic analysis indicates that the carboxylic acid content of the gas feed stream is lowered by the above treatment. At the same time as the concentration of the carboxylic acid is lowered, the lactide content of the stream is increased. The products of this reaction are recovered by passing as a gas into a liquid solvent.

We claim:

1. A continuous catalytic vapor phase process for converting an alpha-hydroxycarboxylic acid or ester to a dimeric cyclic ester, which process comprises:

(i) vaporizing said alpha-hydroxycarboxylic acid or ester and continuously feeding it within a non-reactive carrier gas stream to a reaction zone which contains a solid catalyst effective to oligomerize said alpha-hydroxycarboxylic acid or ester to the corresponding cyclic ester;

(ii) maintaining the reaction zone at a temperature and a pressure which is effective to result in the formation of the cyclic ester from the vaporized said alpha-hydroxycarboxylic acid or ester and maintain it in the vapor phase;

(iii) continuously removing the cyclic ester from the reaction zone within the non-reactive carrier gas stream as the ester is formed; and (iv) recovering the cyclic ester from the gas stream.

2. The process of claim 1 wherein the reaction zone is maintained at subatmospheric pressure.

3. The process of claim 1 wherein the reaction zone is maintained at a pressure of about atmospheric pressure.

4. The process of claim 3 wherein the reaction zone is maintained at an effective temperature in the range of from about 170° to about 270° C.

5. The process of claim 3 wherein the carboxylic material fed to the reaction zone is an alkyl glycolate, the temperature is in the range of about 230° to 260° C. and the cyclic ester recovered from the gas product stream is glycolide.

6. The process of claim 5 wherein the alkyl glycolate is methyl glycolate.

7. The process of claim 5 wherein said alpha-hydroxycarboxylic acid or ester fed to the reactor is lactic acid, the temperature is in the range of about 190° to 230° C. and the cyclic ester recovered from the gas stream is lactide.

8. The process of claim 3 wherein the lactic acid is L-lactic acid and the lactide is L-lactide.

9. The process of claim 5 wherein said alpha-hydroxycarboxylic acid or ester fed is an alkyl lactate and the cyclic ester is a lactide.

10. The process of claim 3 wherein the alkyl lactate is a butyl lactate.

11. The process of claim 9 or claim 10 wherein the alkyl lactate is an alkyl L-lactate and the lactide is L-lactide.

12. The process of claim 3 wherein the catalyst is in the form of solid particles and comprises an oxide, a halogenide and/or a carboxylate of at least one metal of Groups III, IV, V and VIII of the Periodic Table.

13. The process of claim 12 wherein the catalyst comprises an oxide and/or carboxylate of tin, or an oxide of trivalent antimony.

14. The process of claim 12 wherein the catalyst comprises an oxide of titanium, an oxide of silicon, an oxide of aluminum or a mixture thereof.

15. The process of claim 14 wherein the catalyst comprises a silica-alumina.

16. The process of claim 15 wherein the silica content of the silica-alumina is greater than the alumina content.

17. The process of claim 16 wherein the silica content of the silica-alumina is in the range of from about 80 to 90% by weight and the alumina content is about 20 to 10% by weight.

18. The process of claim 3 wherein the catalyst is in the form of solid particles maintained by the gas feed stream as a fluidized bed.

19. The process of claim 12 wherein the catalyst is maintained as a fluidized bed by the gas feed stream.

20. Process of claim 3 where the cyclic ester is recovered from the gas product stream by solvent scrubbing.